United States Patent
Mantell

(10) Patent No.: US 7,938,793 B2
(45) Date of Patent: May 10, 2011

(54) MIXED-GAS INSUFFLATION SYSTEM

(75) Inventor: Robert R. Mantell, Arlington Heights, IL (US)

(73) Assignee: Northgate Technologies, Inc., Elgin, IL (US)

(*) Notice: Subject to any disclaimer, the term of this patent is extended or adjusted under 35 U.S.C. 154(b) by 0 days.

(21) Appl. No.: 12/499,649

(22) Filed: Jul. 8, 2009

(65) Prior Publication Data

US 2009/0270794 A1 Oct. 29, 2009

Related U.S. Application Data

(62) Division of application No. 10/829,485, filed on Apr. 22, 2004, now Pat. No. 7,654,975.

(60) Provisional application No. 60/465,081, filed on Apr. 24, 2003.

(51) Int. Cl.
*A61M 37/00* (2006.01)

(52) U.S. Cl. .......................................................... 604/26
(58) Field of Classification Search .................. 128/203.12–203.29; 604/23–26
See application file for complete search history.

(56) References Cited

U.S. PATENT DOCUMENTS

| | | | | |
|---|---|---|---|---|
| 6,123,075 A | * | 9/2000 | Kirk | 128/205.13 |
| 6,158,434 A | * | 12/2000 | Lugtigheid et al. | 128/204.22 |
| 6,645,197 B2 | * | 11/2003 | Garrison et al. | 606/1 |

* cited by examiner

*Primary Examiner* — Manuel A Mendez

(74) *Attorney, Agent, or Firm* — Brinks Hofer Gilson & Lione

(57) ABSTRACT

A mixed-gas insufflation system for mixing insufflation gases includes a gas supply providing at least two sources of insufflation gas and a mixer system. The mixer system includes a chamber having at least two inlets and at least one outlet. The at least two inlets of the chamber are in fluid communication with the gas supply. The mixer system mixes the at least two sources of insufflation gas.

6 Claims, 12 Drawing Sheets

MIXED-GAS INSUFFLATION SYSTEM

FIELD OF THE INVENTION

The present patent document is a divisional of application Ser. No. 10/829,485, filed Apr. 22, 2004, now U.S. Pat. No. 7,654,975 which claims the benefit of the filing date under 35 U.S.C. §119(e) of Provisional U.S. Patent Application Ser. No. 60/465,081, filed Apr. 24, 2003. All of the foregoing applications are hereby incorporated by reference.

CROSS-REFERENCE TO RELATED APPLICATIONS

The present invention relates to the field of surgical instruments, and in particular, relates to the technology and instrumentation used to achieve pneumoperitoneum during laparoscopy and laparoscopic surgery.

BACKGROUND

Surgeons have used laparoscopic surgery to perform a variety of procedures. By manipulating laparoscopes and video telescopes, surgeons gain a visualization of the abdominal cavity while minimizing tissue and muscle injury that normally accompanies conventional invasive procedures. Compared to conventional surgery, laparoscopy reduces patient trauma, decreases patient recovery time, and yields significant cost savings by reducing post-operative care.

The proper hardware and instrumentation are essential to the performance of laparoscopic procedures. To create a sufficient area for the introduction of a laparoscope and other instruments, the abdominal wall is first raised from the organs enclosed in the abdominal cavity. Separation is conventionally attained by pressurizing the abdominal cavity with an insufflation gas. Typically one insufflation gas, such as carbon dioxide, nitric oxide, nitrous oxide, helium or argon, is used. The presence of artificial gas in the peritoneal cavity to achieve exposure of the cavity during laparoscopy is referred to as pneumoperitoneum.

Studies have shown that different gasses have differing effects on post-surgical healing, pain, and tumor formation. For example, a problem that may occur when using one of the above-named gases to create pneumoperitoneum is hypoxia. Hypoxia is a condition that occurs in the tissues due to a lack of oxygen and may lead to the growth of tumor sites around the surgical area, post-operative adhesions, and cellular decay. If however, oxygen is used to create pneumoperitoneum, there may be problems with embolisms occurring due to air bubbles forming at the surgical site. Moreover, oxygen is a substance that that supports combustion and should be used in lower levels to avoid a flammable environment and yet be used in a large enough quantity to avoid hypoxia.

Normally, the use of two or more insufflation gases will optimize the post-surgical healing process. One approach to achieve this benefit is to use two insufflators so that two insufflation gases, one perhaps being oxygen, may be used. It may, however, be cumbersome to have two insufflators located at the surgical area. Moreover, this method is expensive.

Accordingly, it is desirable to have a device that overcomes the disadvantages and limitations described above.

SUMMARY

In order to address the need for an improved apparatus to provide a mixed composition of insufflation gases, a novel mixed-gas insufflation system is described below. The mixed-gas insufflation system includes a gas supply providing at least two sources of insufflation gas and a mixer system. The mixer system includes a chamber having at least two inlets and at least one outlet. The at least two inlets of the chamber are in fluid communication with the gas supply. The mixer system mixes the at least two sources of insufflation gas.

Another aspect of the invention includes an insufflator having at least two inputs, each for supplying a source of insufflating gas. A mixing chamber is in fluid communication with the at least two inputs and has at least one output. At least one delivery path is attached to the at least one output of the mixing chamber. A central processing unit is electrically connected with the at least one delivery path monitors and controls the flow of insufflation gas passing through the at least one delivery path. At least one output line is attached to the at least one delivery path. The at least one delivery path and the at least one output line allows for the continuous supply of mixed insufflation gas to a surgical site during a laparoscopic procedure.

An additional aspect of the invention includes a mixed-gas insufflation system for mixing insufflation gases. A gas supply provides at least two sources of insufflation gas and mixing means are in fluid communication with the gas supply. The mixing means mix the at least two sources of insufflation gas.

Another aspect of the invention encompasses a method for mixing at least two insufflation gases. The method includes providing at least two sources of pressurized insufflation gases and delivering gas from each source into a tubing system. The flow and pressure of each insufflation gas are controlled within the tubing system. Each insufflation gas is delivered in parallel from the tubing system into a mixing chamber. The at least two sources of insufflation gas are mixed within the mixing chamber and expelled from the mixing chamber through at least one outlet.

For purposes of simplicity and convenience, the mixer system will be described with respect to the insufflation of a peritoneal cavity. One skilled in the art, however, will readily understand that the use of the mixer system is not limited to the insufflation of the peritoneal cavity.

DETAILED DESCRIPTION OF THE PRESENTLY PREFERRED EMBODIMENTS

Disclosed below are various embodiments of a mixing area for providing a mixed insufflation gas during laparoscopic surgery. The mixing area includes at least two inlets for the delivery of insufflation gases for mixing and a chamber for mixing the gases. As will be described in detail below, the mixing area may be embodied in a mixer system 2 external to an insufflator or within the insufflator. In addition, and as will also be detailed below, the insufflation gases may be mixed external to the insufflator after passing through the insufflator.

Figure 1:
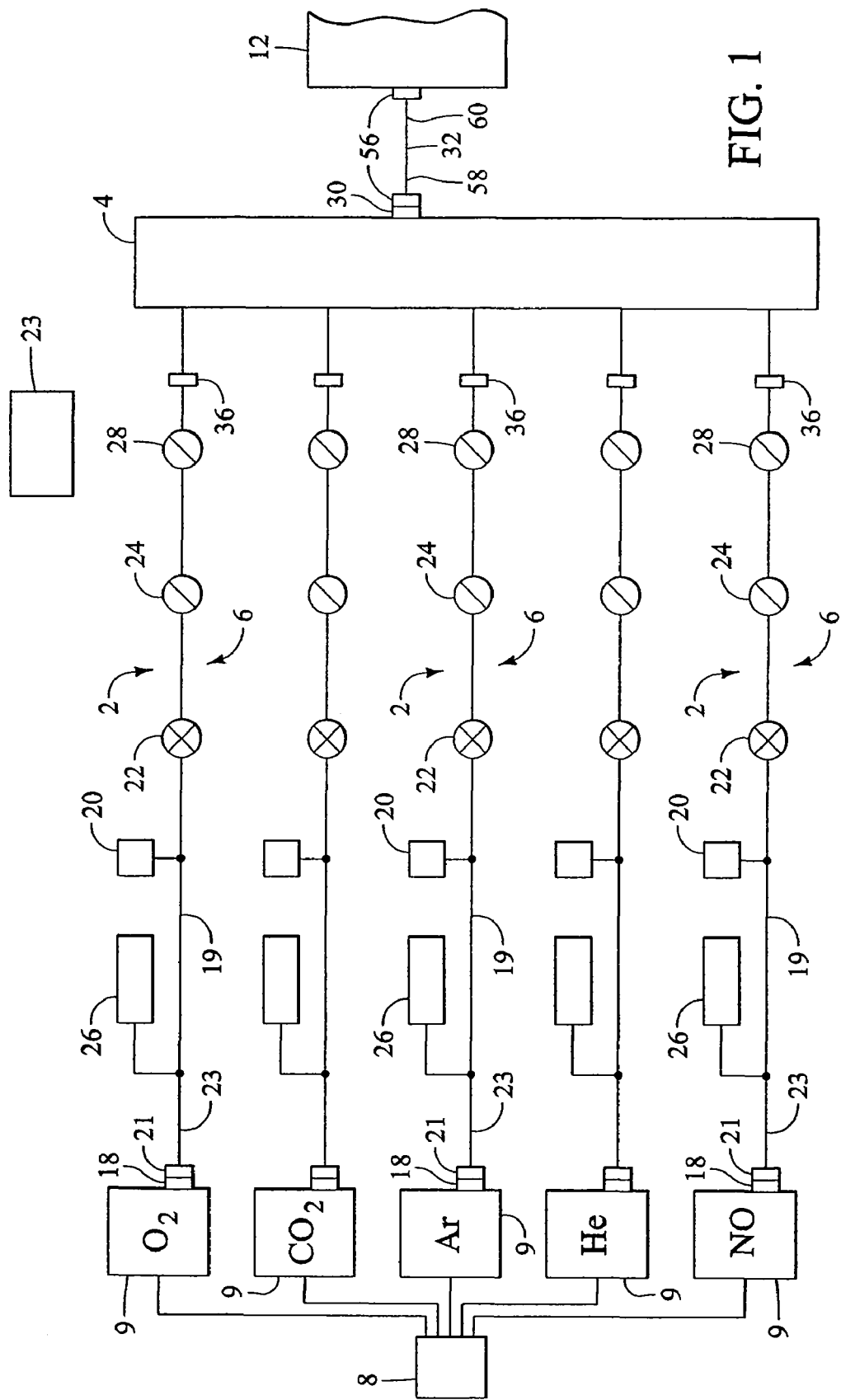
FIG. 1 is a diagram of a first embodiment of a mixer system.
Figure 2:
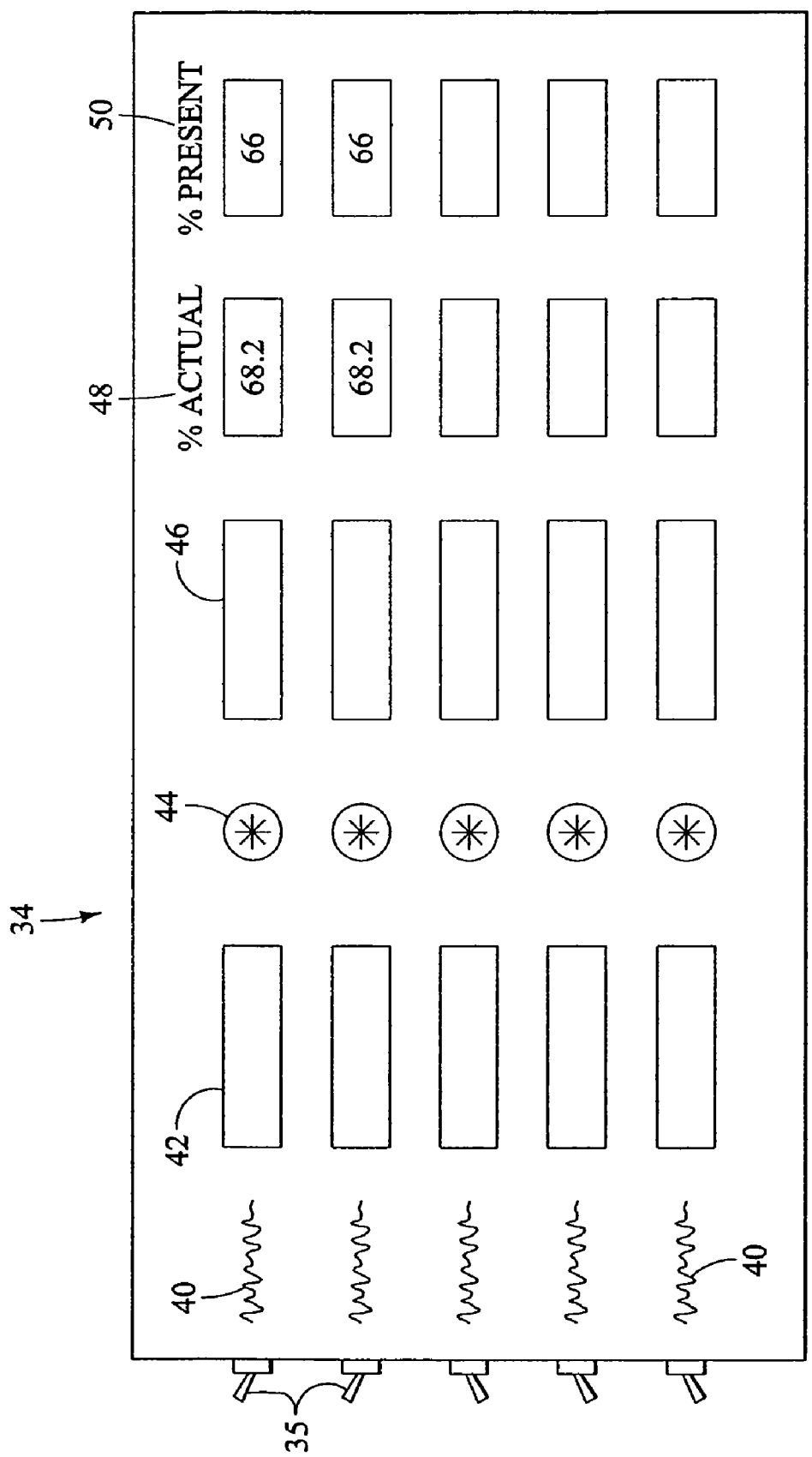
FIG. 2 is a view of a display associated with the mixer of FIG. 1.

Referring to FIGS. 1 and 2, an embodiment of a mixer system 2 for use with an insufflator 12 to provide a mixed insufflation gas during laparoscopic surgery is shown. The mixer system 2 includes a mixing chamber 4, at least two tubing systems 6, and a gas supply 8. As will be discussed further below, the insufflation gas flows via at least one external output line from the insufflator 12 to laparoscopic equipment 260 that is inserted into a peritoneal cavity.

The gas supply 8 provides various insufflation gases for mixing in the mixing chamber 4. The gas supply 8 may be several separate sources 9, or bottles, that each act as a source of an insufflation gas. Alternatively, the gas supply may be a central supply that houses the various insufflation gases.

A variety of insufflation gases may be used. However, so that the tissue affected during a laparoscopic procedure may be oxygenated, which is desirable in order to promote the health and ultimate healing of the tissue, one of the gases preferably is oxygen, although oxygen is not required. In one embodiment utilizing oxygen, oxygen preferably should make up no more than approximately five percent of any gaseous mixture. In other embodiments oxygen may be present in amounts anywhere from approximately five percent through 100 percent of any gaseous mixture, with, of course, the appropriate controls being in place. The amount of oxygen may be varied so long as it is below an amount that supports combustion. Other gases may include, but are not limited to, carbon-dioxide, argon, helium, nitric oxide and nitrous oxide, as well as other inert gases known to be compatible for laparoscopic surgery by those in the art.

The tubing system 6 provides for the fluid communication of insufflating gas, which exits on an outlet 18 on the gas supply 8 and proceeds to the mixing chamber 4. There is one outlet for each source 9, and there is a tubing system 6 associated with each insufflating gas. In one embodiment, the tubing system 6 includes a tube 19, a transducer 20, a pressure regulator 22, a flow valve 24, and a sensor 26. The tube 19 provides for the travel of the insufflating gas from the gas supply 8 to the mixing chamber 4. The tube 19 is a disposable polyvinyl chloride tube, although in other embodiments any suitable materials may be used. For example, in alternate embodiments, the tubing may be made of a silicone material that is reusable, stainless steel, copper, chrome-plated brass or a high-pressure nylon.

A connector 21 on a first end 23 of the tube 19 connects the tubing system to the gas supply 8. Any suitable connector 21 may be used, but the connector 21 should be of a type so the flow capacity of insufflation gas from the gas supply 8 is not restricted. Examples of connectors include, but are not limited to, barb, spring-loaded, or quick-disconnect connectors.

The transducer 20 reads an input pressure of the insufflating gas as it enters the tubing system 6 from the gas supply 8 to determine if a sufficient supply of insufflating gas exists. Whether a supply of insufflating gas is sufficient will depend on surgical requirements and any regulations that are in place. A typical input pressure, however, is generally in the range of 2,000-3,000 pounds per square inch for separate sources such as bottles and approximately 60-100 pounds per square inch for sources supplied via a central supply. If there is an insufficient supply of insufflating gas, the mixing system will be shut down via a CPU 23 associated with the mixer system 2. Further detail about the CPU 23 is provided below. An example of a suitable pressure transducer is a transducer available from ASHCROFT in Stratford, Conn.

Note that a pressure switch, rather than a transducer, may be used in alternate embodiments. The pressure switch may be a standard go/no-go switch. When the switch fails to detect a required, predetermined input pressure, the switch will not allow insufflation gas to pass to the tubing system 6.

The pressure regulator 22 reduces the input pressure of the insufflating gas so that it is suitable for use with the insufflator. Suitable pressures generally are dictated by surgical requirements and any regulations. Generally, however, a suitable pressure for an insufflation gas for use with an insufflator is approximately 60 pounds per square inch. An example of a suitable pressure regulator is supplied by NORGEN in St Littleton, Colo. and is rated at approximately 3,000 PSI.

The flow valve 24 is a normally closed valve that opens when the insufflating gas associated with the corresponding tubing system (and flow valve) is desired for use during laparoscopic surgery. An example of a suitable flow valve is provided by Pneutronics in Hollis, N.H. Preferably, the valve is of a type and size so that it has a rating, or meters out gas at a rate of, approximately 10 pounds per square inch, which assumes a flow rate of approximately 20 liters per minute. In other embodiments, valves having a different rating may be used, depending on the flow rate of the gas.

The flow valve 24 is electronically connected with the CPU 23 associated with the mixer system 2. The CPU 23 is a standard, commercially-available CPU and examples include Northgate's Model 63-13901-2 available from Northgate Technologies, Inc. in Elgin Ill. and CPU Model IND-386S available from Indocomp Systems in Metamora, Mo. When the CPU identifies the presence of an insufflating gas associated with a flow valve 24, it will cause that flow valve 24 to open so that the insufflating gas may enter the mixing chamber 4.

The sensor 26 identifies the presence of the insufflating gas that is associated with the tubing system 6. In other words, the sensor prevents the wrong gas from being connected to a tubing system; i.e., the sensor prevents the situation where a tubing system presumed to be connected to a source of argon gas, for example, is actually connected to a source of carbon-dioxide. If the wrong gas is indeed connected to a tubing system, the CPU will shut down the system. Optionally, there also may be an alarm to indicate that the wrong gas has been connected to a tubing system. As shown in FIG. 1, the sensor may be located along the tube 19. In other embodiments, the sensor 26 may be located within the insufflator 12.

In one embodiment, the sensor 26 is a 100 ohm resistor block that identifies the insufflating gas based on an ohmic value pre-assigned to the insufflating gas. The sensor 26 is electrically connected with the CPU 23. When an insufflating gas is desired, electronics associated with the CPU 23 will identify the presence of the insufflating gas by reading the sensor 26 associated with a particular tubing system 6. As noted above, the CPU 23 will then open the flow valve 24 so that the insufflating gas may flow to the mixing chamber 4.

In alternate embodiments, the sensor may sense voltage or the current drop of the insufflation gas associated with the sensor. In an additional alternate embodiment, sensing may be accomplished mechanically through methods such as mechanical indexing. For example, the threads of each of the connectors 21 may be different from each other so that a connector may only be attached to one gas supply.

Moreover, in yet other embodiments, the sensor may be a gas analyzer. The gas analyzer is used to identify the type of gas associated with a tubing system 6 or may be used to identify the types of gases present within a mixture, as well as the amount of each gas that is present as compared to the whole. For example, if a gaseous mixture of one-third oxygen and two-thirds carbon dioxide is present, the gas analyzer can detect both the gases present and the amounts, one-third oxygen and two-thirds carbon dioxide, that are present. An example of a suitable gas analyzer is the Model 224A Quadralyzer Gas Analyzer made by Raytech Instruments, Inc. in North Vancouver, Canada.

A gas analyzer may be present on each tubing system, in which instance the gas analyzer will be used to detect the type of gas associated with a particular tubing system. Alternatively, the gas analyzer may be located near the output of the mixing chamber 4, in which instance it may be used, as described above, to both detect the types of gases present and to detect the ration of each gas present.

Optionally, and as shown in FIG. 1, a metering valve 28 may be incorporated into the tubing system 6 for redundancy. The metering valve 28 controls the flow of insufflation gas into the mixing chamber 4. The metering valve is electrically connected to the CPU 23. The CPU 23, knowing the molecular weight of a particular insufflation gas, may open or close the metering valve 28 so that the amount of flow, and hence the volume, of insufflation gas passing through the metering valve is controlled. Thus, the metering valve 28 ensures that the desired volume of gas passes from the tubing system 6 into the mixing chamber 4.

A filter 36 normally is located in each tube 19 of each tubing system 6 to provide a particulate barrier. In one embodiment, the filter 36 is a glass-fiber hydrophobic filter that provides a particulate barrier of approximately 25 microns and operates at a ninety-nine percent rate of efficiency. In other embodiments any number of commonly used filters, with different filtering capabilities, may also be used.

The mixing chamber 4 is a standard manifold, such as a hollow tube, cavity, or chamber. Although a hollow tube able to hold three liters of gas is preferred, the mixing chamber 4 may have any size or shape. The mixing chamber 4 may be made from any materials suitable for use with the particular insufflation gases that are to be used. Examples include, but are not limited to, stainless steel, plastics, chrome-plated brass or high-pressure nylon.

Figure 6:
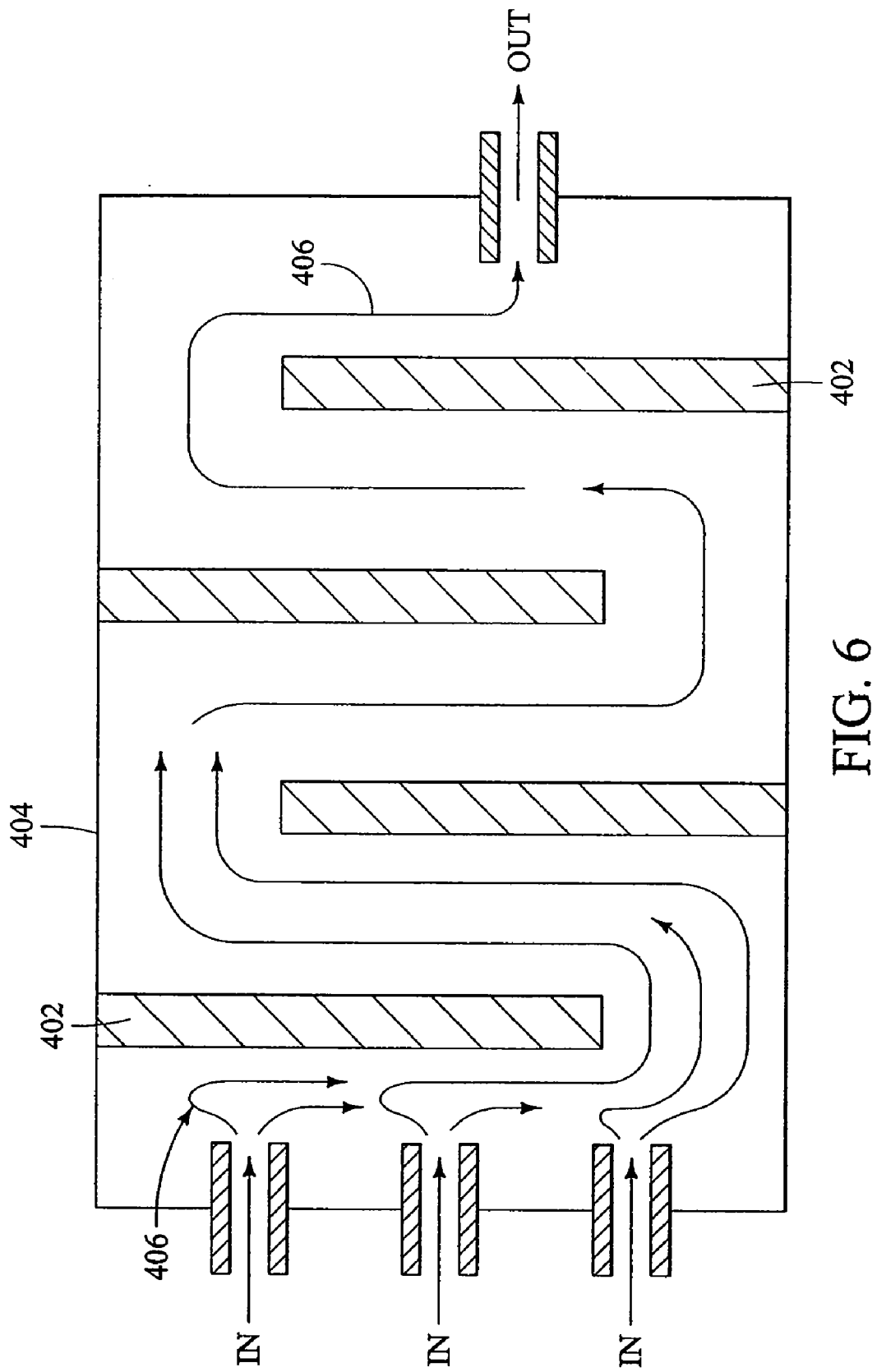
FIG. 6 is a side view of a mixing chamber having baffles.

A purpose of the mixing chamber is to provide an area for the gases dispensed from the gas supply to form a homogenous mix. Because gases each have different properties, with some gases being heavier than others, it may be desirable to incorporate components into the mixing chamber in order to further assist with the mixing of the various insufflation gases. In one embodiment, as shown in FIG. 6, at least one baffle 402 may be incorporated into the mixing chamber 404. The baffle acts as an obstruction within the chamber, created within the path of the gases as they flow through the chamber. The baffle creates turbulence as the gases flow (depicted by arrows labeled as 406) to further facilitate the mixing of the gases.

As noted, there may be at least one baffle, with four baffles being preferable. In other embodiments, a different number of baffles may be used, depending on the gases used and the size of the mixing chamber. The baffles may be of any shape and made of any material compatible with the material of the mixing chamber, including, but not limited to, plastics, various metals, and composite materials.

Figure 7:
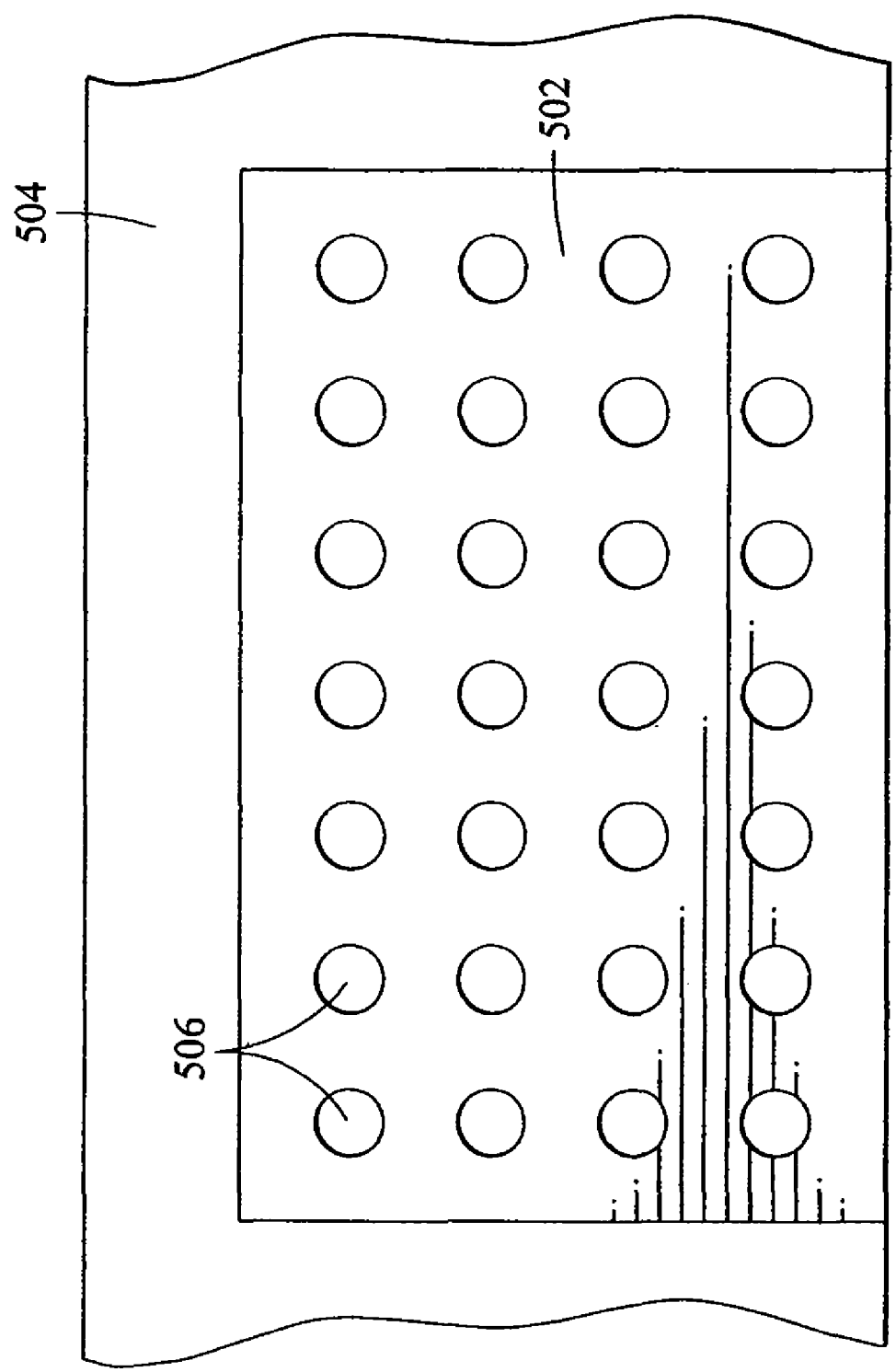
FIG. 7 is a plan view of a mixing chamber having a plate with a plurality of holes.

In an alternate embodiment, as shown in FIG. 7, the mixing of the gases may be facilitated through the use of a plate 402 being incorporated into the mixing chamber 404. The plate 402 includes a series of holes 406, allowing the gases passing through the chamber 404 to both pass through the holes 406 and to be repelled at the parts of the plate not having a hole 406. This motion causes turbulence to be created when the gas hits an area of the plate 402 not having a hole 406, thus further facilitating the mixing of the gases. The mixture of gases may then pass through the output of the chamber.

Figure 8:
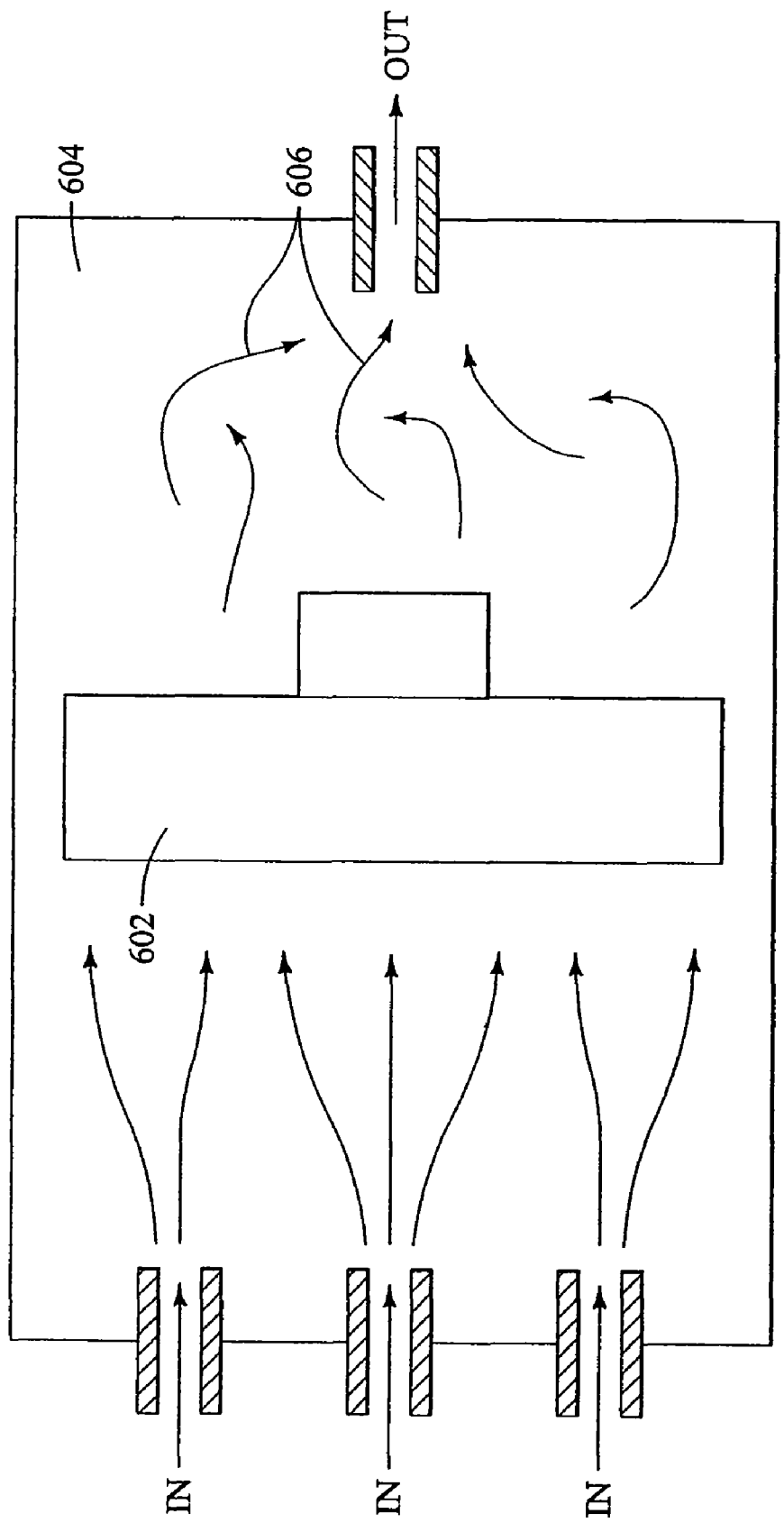
FIG. 8 is a side view of a mixing chamber having a fan.

Referring to FIG. 8, an additional embodiment to further facilitate the mixing of gases with the chamber may include a fan 602 located within the chamber 604. Turbulence is created as the gas passes through the fan, with the turbulent gas depicted by arrows labeled as 606. Any suitable fan 602 may be used that can fit within the chamber. The circulation capacity of a suitable fan will depend on the size of the chamber and the amount of turbulence that is desired. An example of a suitable fan is Orion fan model no. OA825AP-11-1WB, distributed by Main Electronic Supplies Ltd. of Vancouver, B.C. Canada. Moreover, the fan may be incorporated into embodiments that include components such as the baffle or the plate described above.

Although the mixing chamber may receive only one insufflating gas, preferably the mixing chamber will receive at least two insufflating gases for mixing. As will be further detailed below, the gases enter the mixing chamber 4 via the tubing system 6 at a preset pressure. The gases are then "mixed" as a result of expanding within the confines of the mixing chamber 4. The mixed insufflation gas then exits the mixing chamber 4 through at least one outlet 30. The insufflation gas then flows through tubing 32 attached to the outlet 30 to the insufflator 12. The tubing is a disposable polyvinyl chloride, although in other embodiments any suitable materials may be used. For example, in alternate embodiments, the tubing may be made of a silicone material that is reusable, stainless steel, copper, chrome-plated brass or a high-pressure nylon.

When a particular insufflation gas is desired, standard toggle switches 35 (FIG. 2) may be used to select the desired insufflation gas and thus allow gas to flow from the gas supply 8 to the tubing system 6. In alternate embodiments, by way of example, activation may also be accomplished through a remote activation device or by manually connecting the source supply to the tubing system.

FIG. 2 is an example of a display 34 associated with the mixer system 2. Indication on the display 34 may be provided via any standard method such as, by way of example, the use of LEDs (not shown). The display may show the types of insufflation gases available (at 40) and the source pressure 42 of each gas. An active status indicator 44 may also be displayed to indicate which insufflation gases are in use during a laparoscopic procedure. The selection of a desired insufflation gas may be accomplished via methods such as those described above. The display 34 may also indicate the actual volume (at 46) of each gas that is entering the mixing chamber 4.

The percent composition of the mixed insufflation gas may also be displayed. The actual percent composition 48 as well as the preset percent composition 50 may both be displayed so that any fluctuation may be indicated. In the example shown in FIG. 2, the mixed insufflation gas has been preset to be composed of 66% of a first insufflation gas and 34% of a second insufflation gas. The actual composition, however, is 68.2% of the first gas and 31.8% of the second gas. As noted above, the percentage of insufflation gas in a mixture is controlled by the metering valve 28 and CPU 23. Moreover, the percentage of insufflation gas may either be preset or can be varied as required via inputs to the CPU 23.

Figure 3:
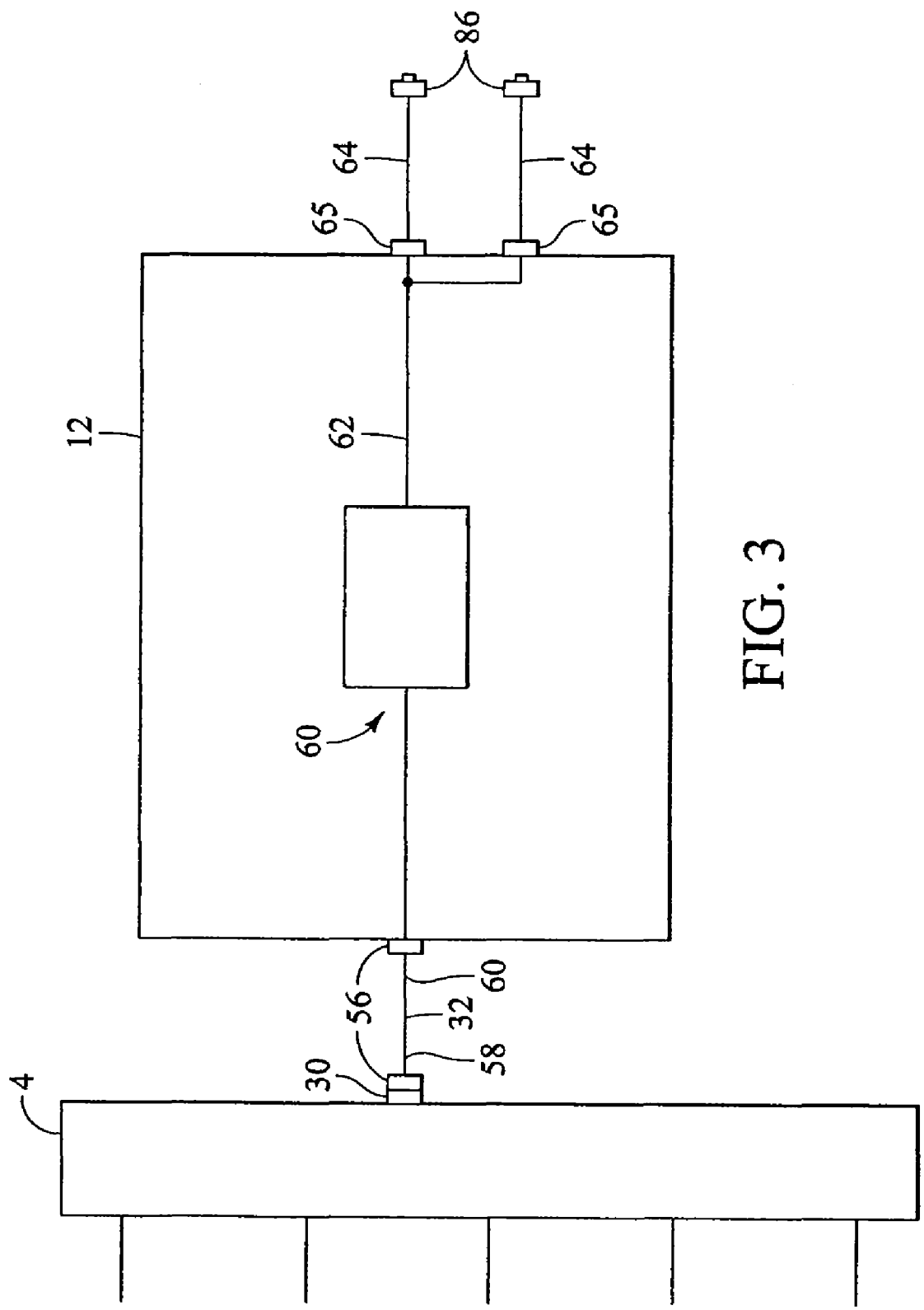
FIG. 3 is a diagram of the mixing chamber supplying insufflation gas to an insufflator.

Referring to FIGS. 1 and 3, and as noted above, upon being mixed in the mixing chamber 4, the mixed insufflation gas exits the mixing chamber 4 via at least one output 30 on the mixing chamber 4. The tube 32 connects the mixing chamber 4 to the insufflator 12. Connectors 56 on first and second ends 58, 60 of the tube 32 connect the tube 32 to the mixing chamber 4 and the insufflator 12, respectively. The insufflator 12 is a standard insufflator, such as the OMNIFLATOR Model 6620 available from Northgate Technologies, Inc. in Elgin, Ill. The insufflator receives the mixed insufflation gas via the tube 32 connecting the insufflator 12 to the mixing chamber 4. The mixed insufflation gas is reduced in pressure by the insufflator to approximately 45 through 55 millimeters of mercury (also know as a "push" pressure), although the pressure may be changed depending on the insufflator in use and any regulations that may be in force. The mixed insufflation gas is delivered via a delivery assembly 60 to at least one output line 62 and passes from the insufflator 12 to at least one tube 64 connected to a port 65 associated with the output line 62. The delivery assembly 60 is mainly comprised of electronics and pneumatics which, as noted above, are standard to the insufflator 12. A trocar connector 86 such as a Leur connector is attached to the tube 64. Laparoscopic equipment (not shown) for insertion into a peritoneal cavity may then be attached to the trocar connector.

Note that in an alternate embodiment, instead of utilizing a separate mixer system, the insufflation gases may be mixed within a chamber in the insufflator 12. The components are similar to those described in associated with the mixing system 2, except that they are located within, rather than separately from, the insufflator. Examples of a suitable insufflator include the OMNIFLATOR Model 6620 described above or the 7600 series model insufflator, also known as a multi-output insufflator, which is described below, also available from Northgate Technologies, Inc.

Figure 4:
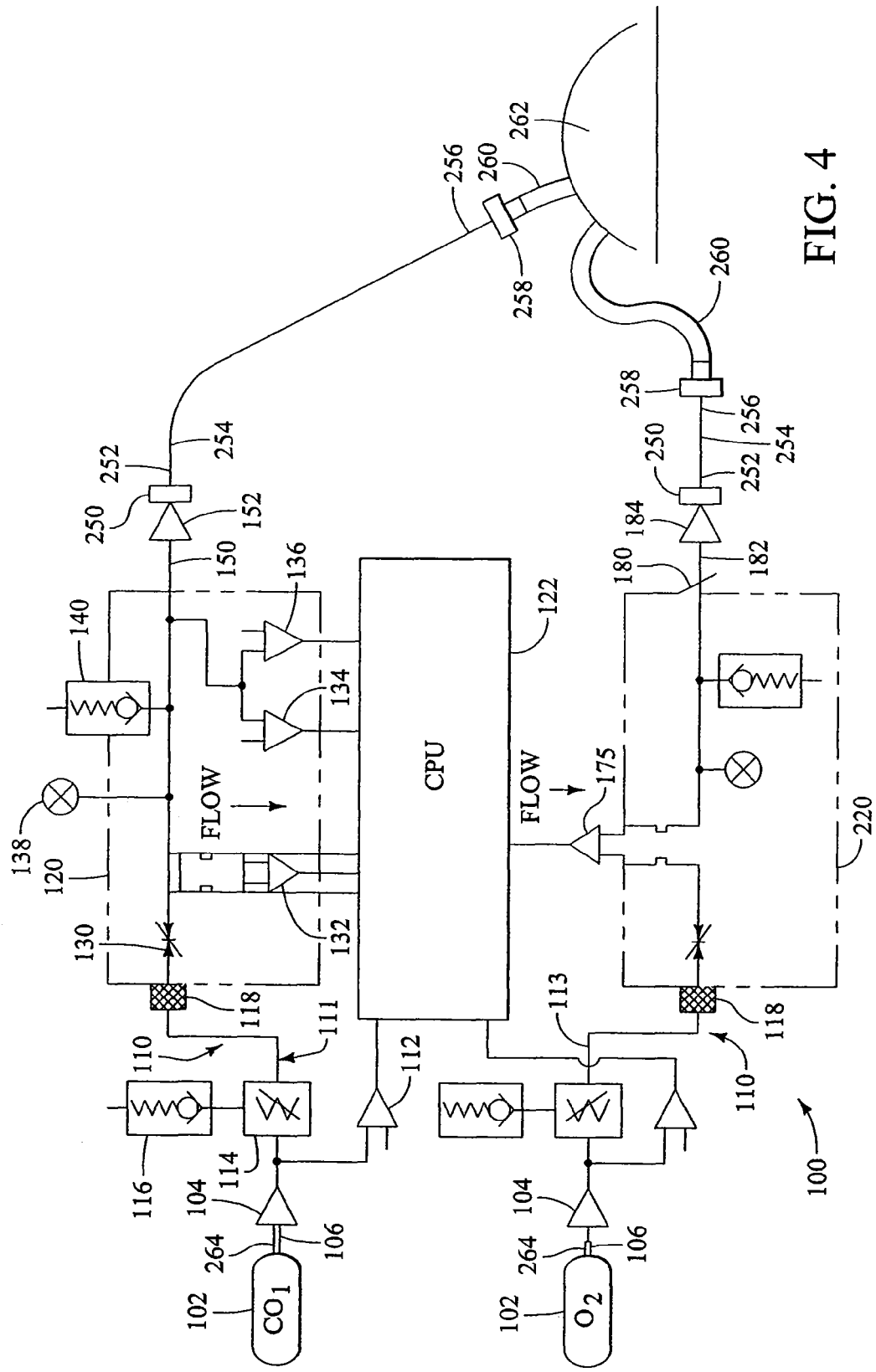
FIG. 4 is a diagram of a second embodiment of a mixing chamber incorporated into a multi-output insufflator.
Figure 5:
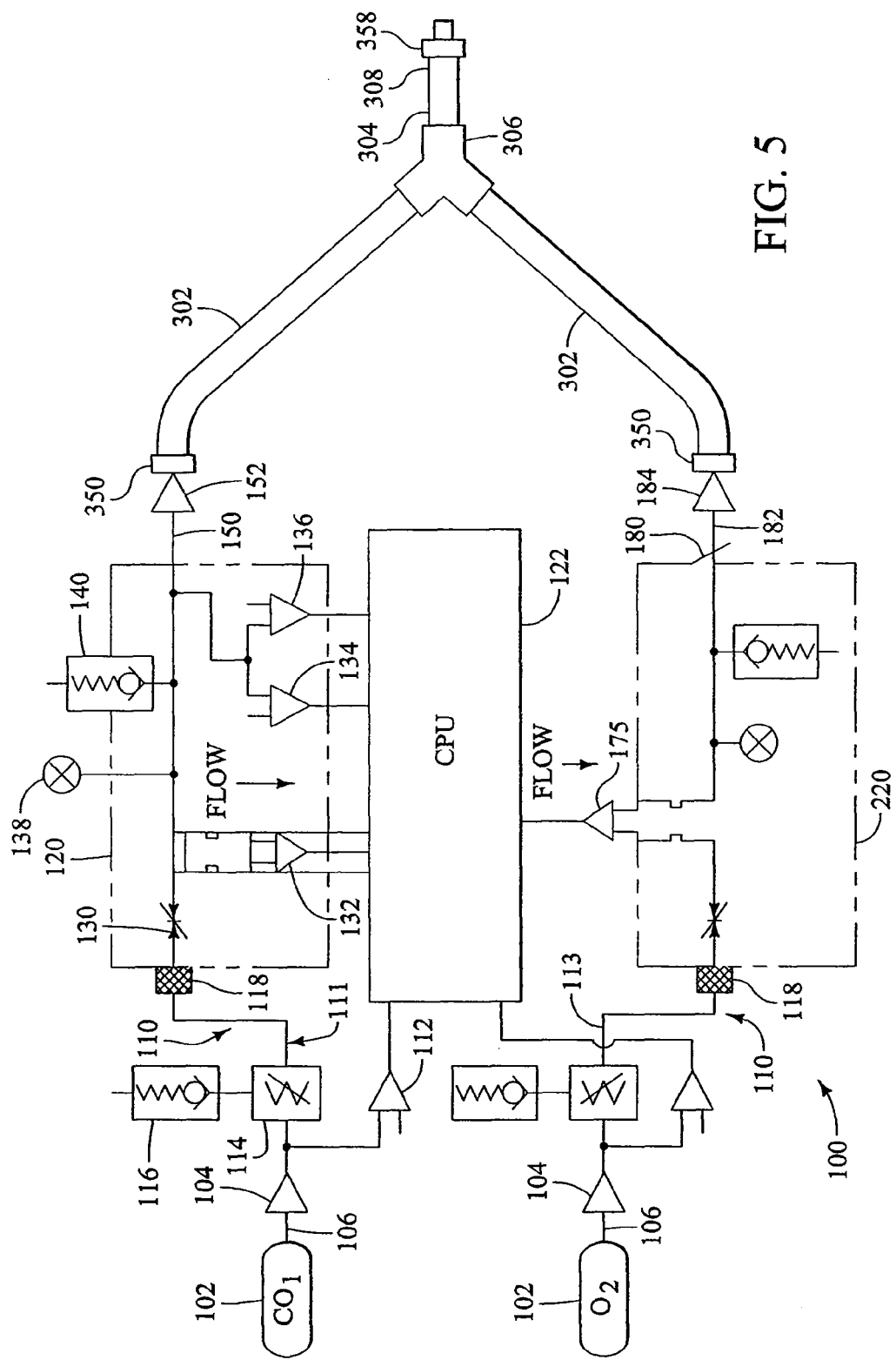
FIG. 5 is a view of an insufflator and dual-capacity tube.

In yet an alternate embodiment, the insufflation gases may be mixed external to the insufflator after passing through the insufflator. An example of such a suitable insufflator is the 7600 series model insufflator, also known as a multi-output insufflator, also available from Northgate Technologies, Inc. This type of insufflator is also embodied in U.S. Pat. No. 6,299,592, issued Oct. 9, 2001, and is herein incorporated by reference in its entirety. A schematic diagram of the multi-output insufflator 100 is shown in FIG. 4. At least two gas sources 102 are connected to inputs 104 on the insufflator 100. The sources are connected to the insufflator 100 via tubing 106 and connectors such as those described above.

Upon entry into the insufflator 100, each insufflation gas enters a delivery path 110. Although there may be more than two delivery paths 110, for simplicity an insufflator having two delivery paths, a primary and a secondary delivery path 111, 113, will now be described. The delivery paths 111, 113 are virtually identical, with differences being noted below. The delivery path 111 includes a supply pressure sensor 112, a regulator 114, a pressure relief valve 116, a filter assembly 118, and a manifold 120. The supply pressure sensor 112, or pressure-measuring transducer, monitors gas supplied by the gas source 102. The pressure-measuring transducer 112 communicates with a controller or microprocessor (CPU) 122 to indicate the amount of gas available for insufflation.

The regulator 114 and the pressure relief valve 116 monitor the delivery pressure of the delivery path 110 of insufflating gas. Operation of the regulator 114 and pressure relief valve 116 are statically controlled. The pressure regulator 114 is serially connected to the static pressure relief valve 116 and both have operating values that are selected to provide a proper operating pressure for a given laparoscopic procedure, typically about 55 pounds per square inch.

The filter assembly 118 provides a particulate barrier down to approximately 20 microns, although in other embodiments a filter with a different rating may be used. As shown, the manifold 120 is attached to the filter assembly 118 by an air tight connection 122. The manifold 120 is comprised of a flow control valve 130, an internal flow sensor 132, primary and secondary internal pressure sensors 134, 136, and a plurality of pressure relief valves 138, 140. The manifold 120 also includes a primary gas output channel 150 that terminates at a primary gas output connector 152.

The flow control valve 130 controls the flow of insufflation gas from the filter assembly 118 into the manifold 120 in response to the CPU 122. The CPU 122 communicates to the flow control valve 130 in response to measurements sampled from components that include the internal flow sensor 132, the primary and secondary internal pressure sensors 134, 136 and, as will be further detailed below, an internal pressure sensor 175 associated with the secondary delivery path 113.

The gas flow rate in the manifold 120 is calculated by the CPU 122 in response to the signal received from the internal flow sensor 132. The internal flow sensor 132 communicates to the CPU 122 the relative flow rate through a primary precision orifice 142 that provides a gas flow path within the manifold 120.

The primary and secondary internal pressure sensors, or transducers, 134, 136 sample the internal pressure within the manifold 120. The primary and secondary internal pressure sensors 134, 136 are in communication with the CPU 122. Two pressure-measuring transducers 134, 136 are used in order to provide redundant pressure calculations.

The manifold 120 further includes the pressure relief valve 138, which is a digitally responsive primary pressure relief valve that controls the internal pressure of the primary gas output channel 150 by responding to the CPU 122. The CPU 122 communicates to the digitally responsive primary pressure relief valve 138 in response to one of the two pressure-measuring transducers 134, 136. A static pressure relief valve 140 connected to the primary gas output channel 150 provides further redundant pressure control.

As noted above, the components that define the secondary delivery path 113 are similar to the components that define the primary delivery path 111, and therefore, only the differences will be described. The secondary delivery path 113 uses a single pressure-measuring transducer 175 located within the manifold 220. Redundant monitoring of the secondary delivery path 113 is achieved by the CPU's 122 pressure comparisons of the pressure measurements sampled from the primary internal pressure sensors 134, 136, as noted above.

A flap valve 180 is slidably attached between the secondary gas output channel 182 and the secondary gas output connector 184. When only the primary gas output channel 150 is engaged, the flap valve 180 is closed and blocks the secondary gas output channel 182. The closure of the secondary gas output channel 182 causes a substantial pressure build up in the manifold 220. When the CPU 122 detects a substantial pressure build up in the manifold 220 by sampling the output of the internal pressure sensor 175, the CPU 122 recognizes that the secondary output connector 184 is not engaged. When the secondary output connector 182 is engaged, the flap valve 180 is swung to an open engagement subjecting the manifold 220 to the pressure passed by the flow control valve 130.

An external line connector 250 is connected to each gas output connector 152, 184. A first end 252 of an external output line 254 is attached to the external line connector 250. The gas output connectors 152, 184 and the external line connectors 250 are designed to provide an air tight junction between the gas output channels 150, 182 and the external output line 254. The external output line 254 provides for the fluid communication of an insufflating gas between the insufflator 100 and laparoscopic equipment 260 that is inserted into a peritoneal cavity 262. A second end 256 of the external output line 254 has a trocar connector 258 such as a Leur connector attached to it so that laparoscopic equipment 260 may be attached to the external output line 254.

Once the insufflation gases are processed by the insufflator 100, so that they exit at an appropriate pressure and rate of flow, they pass through the external output line 254, trocar 258, and laparoscopic equipment 260 and into the peritoneal cavity 262. Because the insufflator has at least two separate delivery paths, and thus at least two separate external output lines, two different gases may be introduced into the peritoneal cavity 262. The mixing of the gases then occurs within the peritoneal cavity 262. Alternatively, the mixing of the gases may be mixed within a mixing chamber whose inlets are attached to the output line 254 of the insufflator and whose output line(s) are attached to tubing, a trocar and laparoscopic equipment for insertion into the peritoneal cavity 262.

The external output lines 254 should be made from a flexible material, such as, by way of example, disposable polyvinyl chloride tubing. In other embodiments, however, any suitable materials may be used. For example, the external output lines may be made of a silicone material that is reusable.

As with the mixer system 2, when a particular insufflation gas is desired, toggle switches 264 may be used to select the desired insufflation gas. In alternate embodiments, by way of example, activation may also be accomplished through a remote activation device or by manually connecting the source supply to the tubing system. Moreover, as with the mixer system 2, inputs to the CPU 122 may allow the percentage of gas making up a mixture to either be preset or controlled.

In an alternate embodiment, and as shown in FIG. 4, a dual-capacity tube 300, rather than separate external output lines, may be used with the insufflator 100. An example of such a tube is embodied in provisional patent application 60/421,662, filed, Oct. 28, 2002, and herein incorporated by reference in its entirety. The dual capacity tube 300 has a pair of tubes 302 and a mixing tube 304. The pair of tubes 302 and mixing tube 304 are attached via an adaptor 306, such as a stepped or barbed adaptor.

Each of the pair of tubes 302 is attached to an external line connector 350 which, as noted above, is connected to a gas output connector 152, 184 associated with a delivery path 110 of the insufflator 100. Thus, because a different insufflating gas is passing through each delivery path of the insufflator, a different insufflating gas will enter each of the pair of tubes 302. Upon entering the mixing tube 304, the insufflating gases will then be mixed. As with the external output line described above, an end 308 of the mixing tube 304 has a trocar connector 358 such as a Leur connector attached to it so that laparoscopic equipment 360 may be attached for insertion into the peritoneal cavity as described above.

To achieve the greatest benefits of a higher flow rate, the inner diameter of the mixing tube 304 should be at least as large as the inner diameter of each of the pair of tubes 302. Moreover, the mixing tube 304 should be sized so that it is compatible with trocar connectors and laparoscopic equipment.

The dual-capacity tube 300 should be made from a flexible material, such as disposable polyvinyl chloride tubes, although in other embodiments any suitable materials may be used. For example, the tubing may be made of a silicone material that is reusable.

While the above embodiment contemplates the use of one dual-capacity tube, in other embodiments multiple dual-capacity tubes may be used. For example, four delivery paths associated with the insufflator may be used, requiring four gas sources and four external output lines. Thus, two dual-capacity tubes may be used to accommodate the four separate outputs of insufflation gas.

Figure 9:
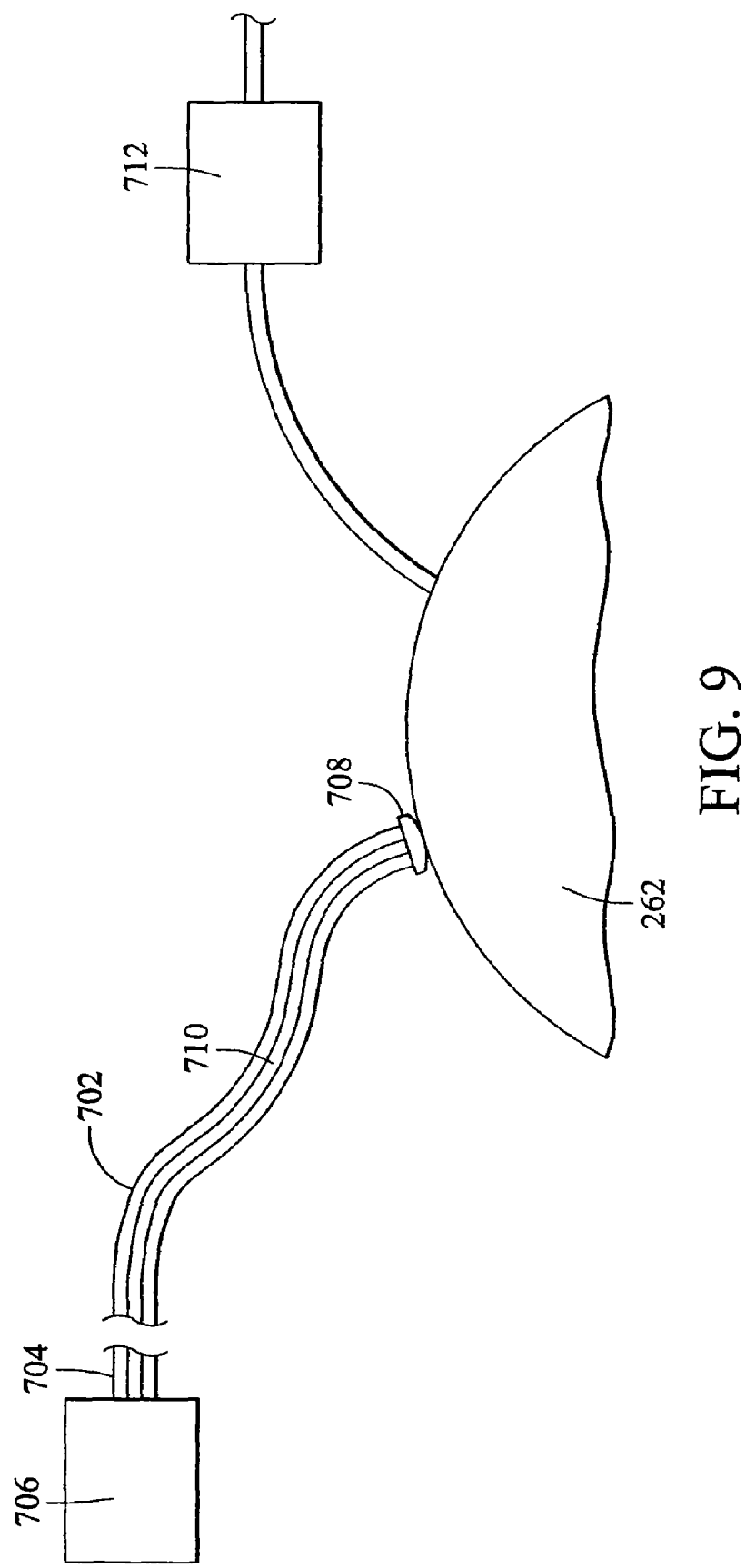
FIG. 9 is a view of a mixer system utilizing a catheter with the catheter in cutaway view.
Figure 10:
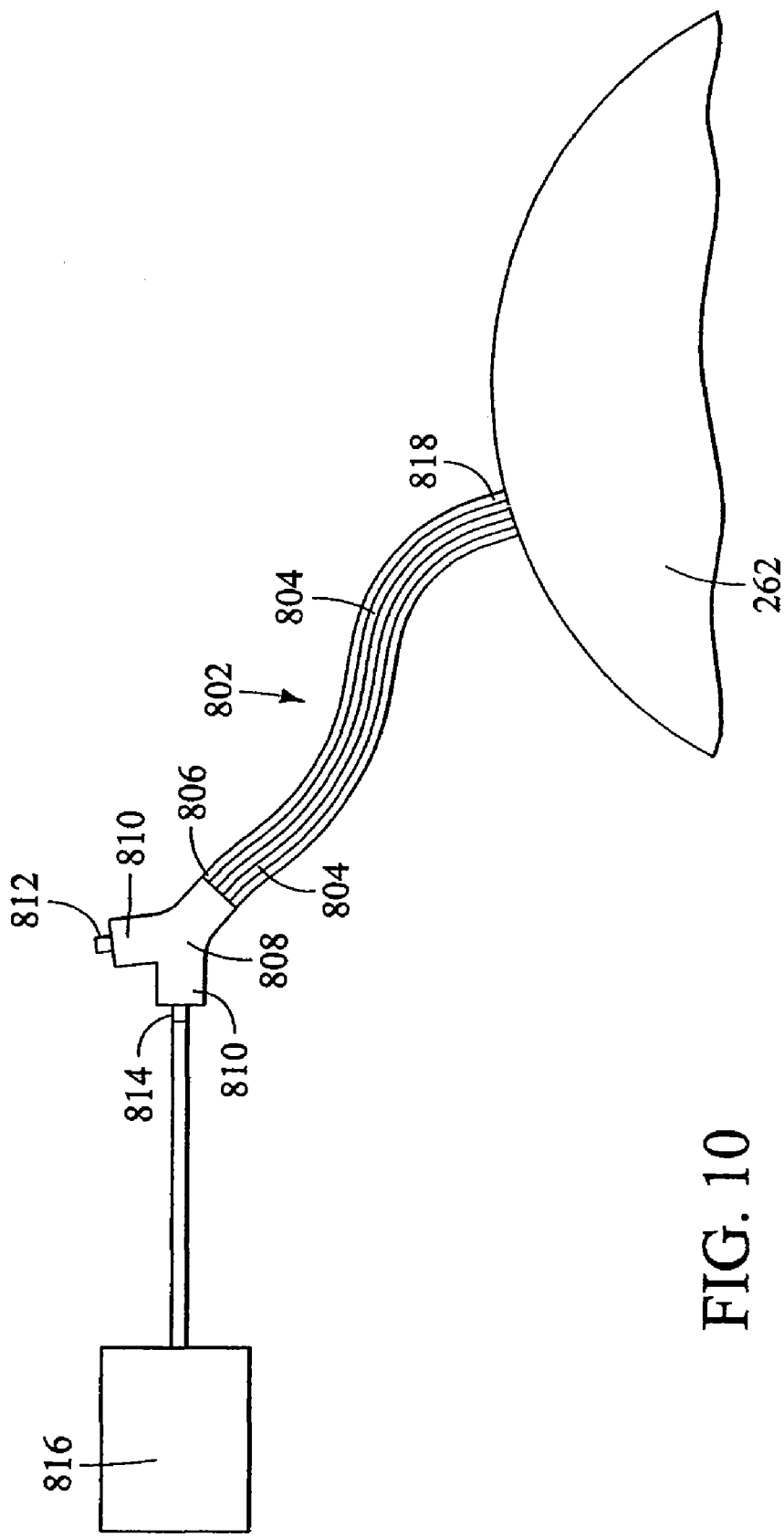
FIG. 10 is a view of a mixer system utilizing a multi-lumen catheter with the catheter in cutaway view.
Figure 11:
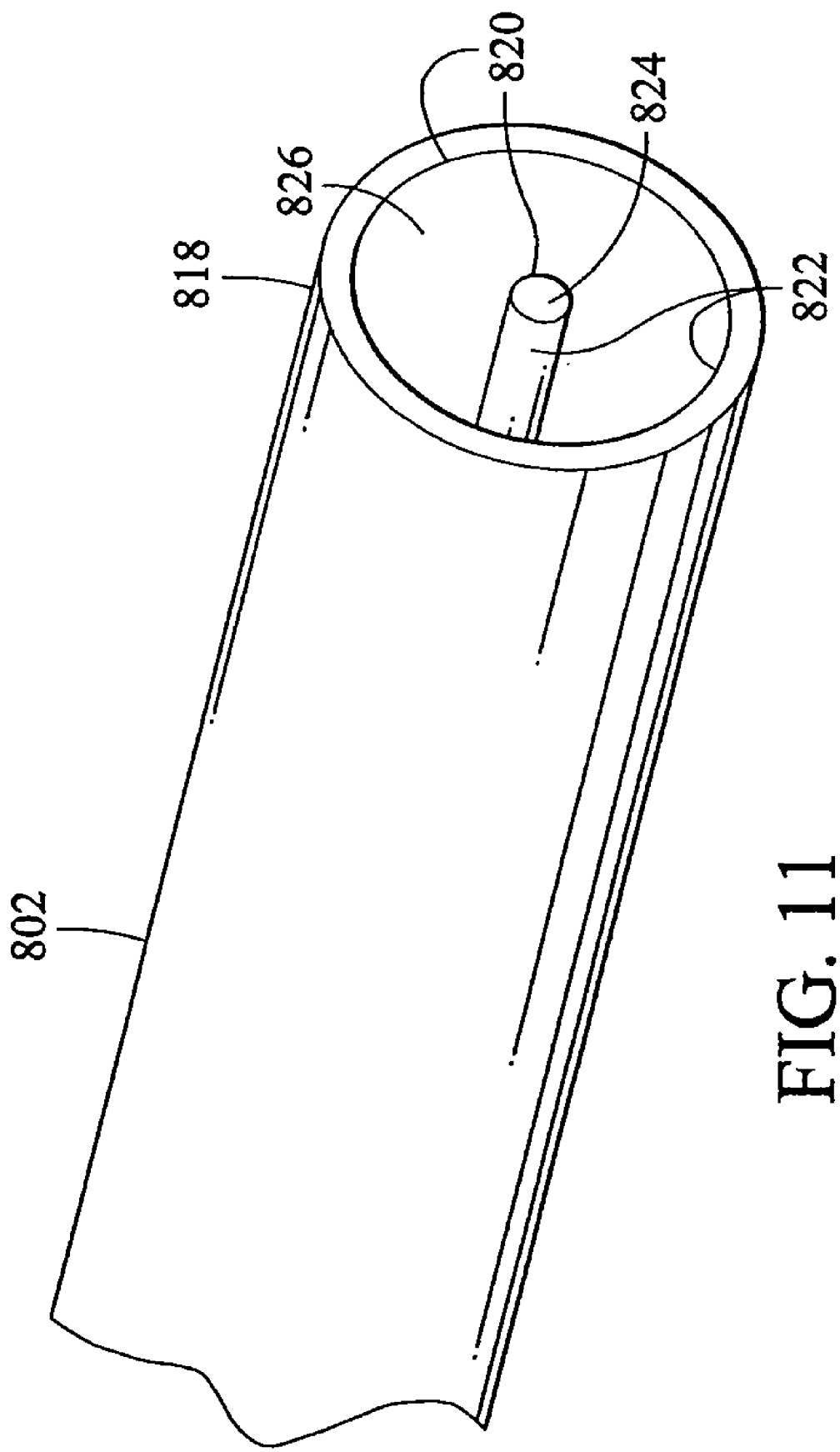
FIG. 11 is a plan view of the outlet of a multi-lumen catheter.

In an additional embodiment, shown in FIG. 9, a catheter may be incorporated to deliver gas into the peritoneal cavity 262. In one embodiment, a single-lumen catheter 702, known to those skilled in the art, is attached at a proximal end 704 to a supply of an aerosolized gas 706. The aerosolized gas usually will include a medication for the treatment of a disease or condition affecting the area targeted for treatment with the gas. A distal end 708 of the catheter is configured for disposition within the peritoneal cavity 262. A lumen 710 runs between both ends and allows the aerosolized gas to pass from the supply and into the peritoneal cavity 262. Simultaneously, gas that has been mixed within the mixing chamber 712 may also be introduced into the peritoneal cavity 262, with the mixing chamber taking on any of the configurations with respect to the insufflator that are described above. The mixing between the aerosolized gas 706 and the gas from the mixing chamber 712 may then occur within the peritoneal cavity 262.

In another embodiment, shown in FIG. 10, a multi-lumen catheter 802 may be used to deliver medication to a patient. An example of such a catheter is embodied in U.S. Pat. No. 5,964,223, issued Oct. 12, 1999, and herein incorporated by reference in its entirety. The multi-lumen catheter 802 includes a plurality of lumens 804. The multi-lumen catheter 802 includes a proximal end 806 having a manifold 808 with at least two inputs 810. At least one of the inputs 812 is attached to a source of liquid medicine (not shown). Such a source is often manifested as a syringe pump. At least one of the other inputs 814 is attached with at least one source of pressurized gas. In this embodiment, the source of gas is the gaseous mixture that has been mixed within the mixing chamber 816, in accordance with the embodiments described above. Each input is attached to a lumen 804 within the catheter. A distal end 818 of the catheter 802, as with the single-lumen catheter, may be inserted into the peritoneal cavity 262.

Referring to FIG. 11, the distal end 818 of the catheter includes a plurality of outputs 820, with an output 820 being in fluid communication with each lumen 822. Liquid passing from the source of liquid medicine will pass through the catheter and exit a first output 824. The pressurized gas will pass through the catheter and exit a second orifice 826. As the pressurized gas passes through the second orifice, it will cause the liquid medicine simultaneously passing through the first orifice to be aerosolized. This will cause the medicine to treat the area targeted for treatment in nebulized form. Note that the outputs and lumen may be configured in a plurality of ways in order to further direct the nebulized medicine. For example, FIG. 11 shows the proximal end having the lumen 820 in a coaxial configuration. Alternatively, by way of example, the lumen may be positioned in a side-by-side configuration. As with embodiments utilizing the single-lumen catheter, the mixing chamber taking on any of the configurations with respect to the insufflator that are described above.

Figure 12:
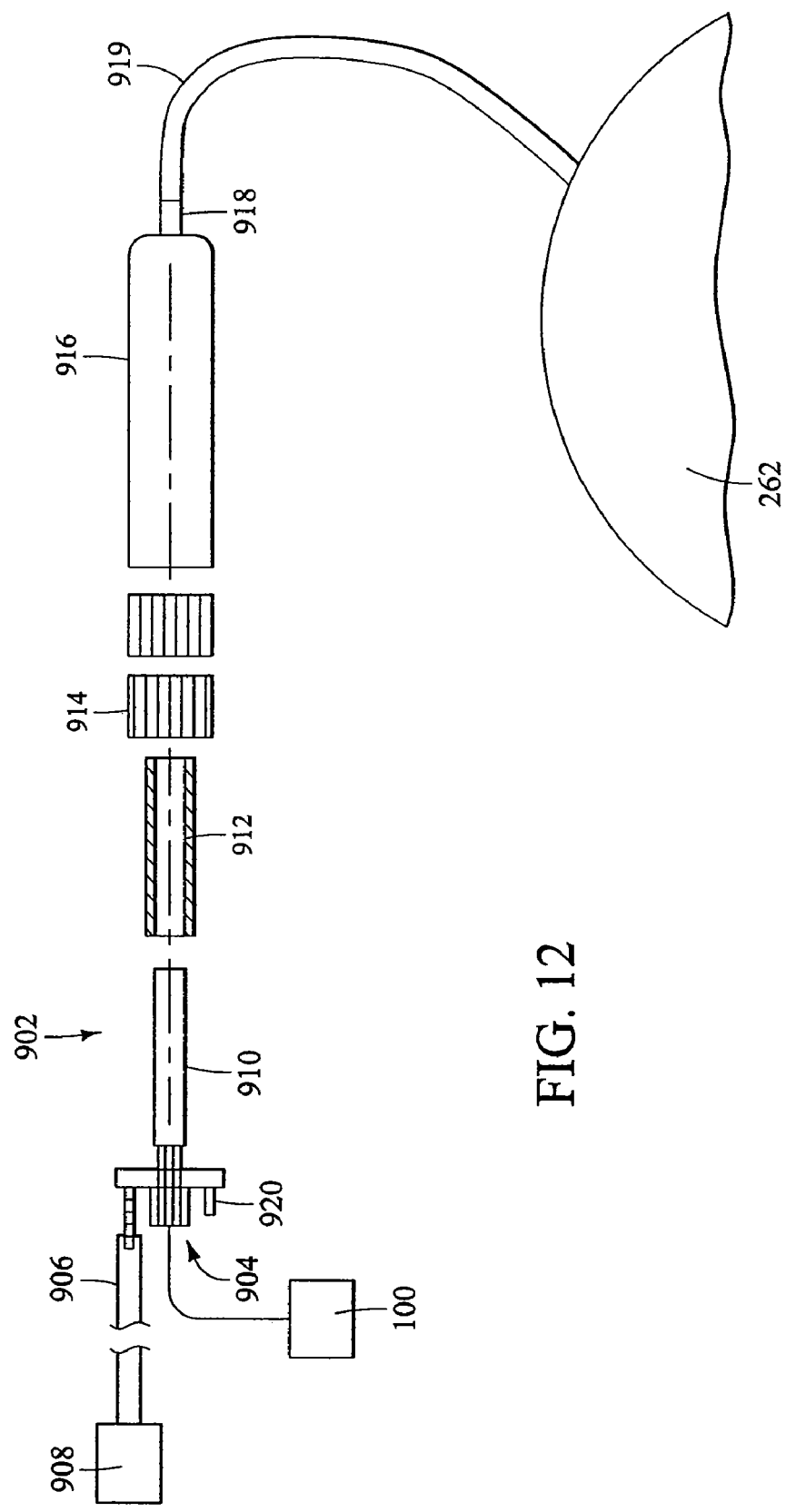
FIG. 12 is a view of a mixer system utilizing a humidification system.

In another embodiment, shown in FIG. 12, insufflation gas that has been mixed within the mixing chamber may then pass through a humidification system 902 so that humidified gas may enter the peritoneal cavity. An example of a suitable humidification system is embodied in U.S. application Ser. No. 09/896,821, filed Jun. 29, 2001, and herein incorporated by reference in its entirety. The humidification system includes a first end 904 that is attached to tubing 906. The tubing supplies insufflation gas that has been mixed in the mixing chamber 908, with the mixing chamber having any of the configurations with respect to the insufflator as described above. The humidification system includes a heater 910, a core 912 surrounding the heater to provide a water-tight environment for the heater, and a humidification material 914 surrounding the core 912. A second end 916 includes an outlet 918 for humidified gas to pass through. The gas may then be supplied through tubing 919 and into the peritoneal cavity 262.

The heater 910 heats moisture that is applied to the humidification material 914. Preferably, the heater has approximately 10 and 50 watts of power, although other wattages may be used depending on the amount of humidity desired. The humidification material 914 surrounds the heater 910 and both absorbs moisture and releases it when exposed to a dry environment. Any suitable material may be used for the humidification material, with examples including nylon and cotton. Examples of manufacturers of humidification material are Pall Medical located in East Hills, N.Y. and Filtrona Richmond Inc. located in Richmond, Va.

The moisture applied to the humidification material is applied via a port 920 for the infusion of fluid for the production of moisture. The moisture may contain medications or other additives that will evaporate and be carried along in the humidified gas to the patient. Moisture may include sterile water, medication, and/or a mixture of fluids required for merely humidifying the insufflation gas.

When insufflation gas, which has been mixed in the mixing chamber 908, enters the humidification system 902 and passes over the humidification material 914, moisture that has been absorbed is released into the insufflation gas, thus humidifying and warming the gas. The warmed and humidified insufflation gas then exits the humidification system through the output 918. The gas may then enter tubing 919 for delivery into the peritoneal cavity 262.

With any of the above-described embodiments, the insufflation gases may, during a laparoscopic procedure, be steadily supplied and mixed throughout the procedure. Alternatively, by way of example, one gas may be steadily supplied while another gas is supplied only sporadically as desired. This could be accomplished through the activation methods described above.

The advantages associated with the mixer system and its associated embodiments are numerous. Normally, because only one insufflation gas can be used during a laparoscopic procedure, an insufflation gas lacking oxygen is generally used. The lack of oxygen to the surgical site may cause hypoxia in the affected tissues. Hypoxia is a condition that occurs in the tissues due to a lack of oxygen and may lead to the growth of tumor sites around the surgical area, post-operative adhesions, and cellular decay. If however, oxygen is used to create pneumoperitoneum, there may be problems with embolisms occurring due to air bubbles forming at the surgical site. Moreover, oxygen is a substance that supports combustion and therefore should be used in lower levels to avoid a flammable environment and yet be used in a large enough quantity to avoid hypoxia.

The mixer system and its alternate embodiments described above allow more than one insufflation gas to be used. A mixture of two or more gases will optimize the post-surgical healing process. Thus, for example, tissues may receive the benefit of an oxygen-rich environment and yet be able to avoid the problems described above that involve the use of high levels of oxygen. Moreover, because the percentages of gas used may be adjusted, if desired, a gas lacking oxygen may first be used during surgery, thus avoiding a flammable environment. Oxygen may then be introduced sporadically as desired to avoid hypoxia and provide affected tissues with oxygen.

While the above description constitutes the presently preferred embodiments of the invention, it will be appreciated that the invention is susceptible of modification, variation, and change without departing from the proper scope and fair meaning of the accompanying claims.

I claim:

1. A mixed-gas insufflator, comprising:
    a housing having at least two inlets for receiving sources of gas;
    a tubing system in fluid communication with each inlet;
    a mixing chamber internal to the housing and having at least two inlets and at least one outlet, wherein the at least two mixing chamber inlets are in fluid communication with the tubing system and the at least one mixing chamber outlet for providing a gas mixture for introduction into a cavity; and
    wherein all gases to be mixed and used to insufflate the cavity pass through the mixing chamber, and wherein the tubing system further comprises a first sensor for sensing whether a predetermined supply of the gas mixture is present and a second sensor for identifying gases comprising the gas mixture to be associated with the tubing system.

2. The mixed-gas insufflator of claim 1, wherein the chamber further comprises at least one baffle.

3. The mixed-gas insufflator of claim 1, wherein the chamber further comprises a plate having a plurality of holes.

4. The mixed-gas insufflator of claim 1, wherein the mixing chamber further comprises a fan.

5. The mixed-gas insufflator of claim 1, wherein the at least two sources of gas are pressurized.

6. The mixed-gas insufflator of claim 1, wherein the at least two sources of gas include oxygen.

* * * * *